United States Patent [19]
de Troostembergh et al.

[11] Patent Number: 4,980,282
[45] Date of Patent: Dec. 25, 1990

[54] TREATMENT OF CORN STEEP LIQUOR

[75] Inventors: Jean-Claude de Troostembergh, Tielt Winge; Francoise Oudeene, Brussels, both of Belgium

[73] Assignee: CPC International Inc., Englewood Cliffs, N.J.

[21] Appl. No.: 122,977

[22] Filed: Nov. 19, 1987

[30] Foreign Application Priority Data

Dec. 15, 1986 [GB] United Kingdom ................. 8629913

[51] Int. Cl.$^5$ ........................ C12P 37/00; C12P 35/06
[52] U.S. Cl. ........................................ 435/43; 426/49; 426/53; 435/139; 435/252.9; 435/813
[58] Field of Search ............. 435/139, 813, 43, 252.4, 435/252.9, 253.4; 426/53, 54, 18, 49; 127/68

[56] References Cited
U.S. PATENT DOCUMENTS

| | | |
|---|---|---|
| 2,232,555 | 2/1941 | Musher . |
| 2,298,623 | 10/1942 | Jurgensen et al. . |
| 2,444,176 | 6/1948 | Thomas et al. . |
| 4,086,135 | 4/1978 | Balana et al. ........................ 435/275 |
| 4,302,475 | 11/1981 | Shigehiro ............................. 426/53 |
| 4,359,528 | 11/1982 | Devos et al. . |
| 4,771,001 | 9/1988 | Bailey et al. ........................ 435/139 |

OTHER PUBLICATIONS

Wang et al, Fermentation and Enzyme Technology, John Wiley & Sons, New York, (1979), pp. 98-109, 116-119 and 128-131.

Primary Examiner—Sam Rosen
Attorney, Agent, or Firm—Rockey and Rifkin

[57] ABSTRACT

A process for the treatment of corn steepwater. The steepwater is incubated for a sufficient time to develop biomass before corn steepwater is fed continuously to the developed biomass at a rate such that the residence time of the steepwater in contact with the biomass is in excess of 4 hours.

6 Claims, No Drawings

TREATMENT OF CORN STEEP LIQUOR

FIELD OF THE INVENTION

The present invention relates to corn steep liquor and to a process for improving the quality of corn steep liquor.

BACKGROUND OF THE INVENTION

"Corn steep liquor" is the name given to the aqueous liquid which is obtained when corn (maize) is digested with warm water so as to soften and swell the corn grain. At the same time, soluble material in the grain is extracted into the steepwater and this material is, given the appropriate conditions, readily fermentable.

In practice, the corn is held in a series of silos through which passes the steepwater. The content of solubles in the steepwater increases as it passes through the series, the water leaving the last silo having the highest content of dissolved matter. The conditions under which the steeping is conducted are conducive to a lactic fermentation taking place in which reducing sugars are converted to lactic acid. As the corn steepwater leaves the last silo, this lactic fermentation is already in progress.

The corn steep liquor being rich in nutrients finds a use as a feedstock for the organisms used in the industrial production of antibiotics, such as penicillin. For this purpose, the corn steepwater from the steeping is submitted to an evaporative process to remove some of the water and thereby concentrate the desired nutrient solids.

It is important that the corn steep liquor used by the fermentation industry has a constant quality. Factors by which the quality is judged are a low content of reducing sugars, a high lactic acid content and a light brown color. The presence of high levels of reducing sugars in the corn steepwater gives rise to the formation of toxic compounds during the evaporation and sterilization of the corn steepwater thereby reducing the yield from a subsequent fermentation.

The use of corn steep liquor as a penicillin nutrient is also unsatisfactory if the liquor has a too high free lysine content. The lysine content of corn steep liquor is diminished to some extent by the fermentation processes taking place in the water during the steeping process but the disappearance of free lysine is slow and the amount left in the corn steep liquor solids after evaporation is frequently too high for their use in penicillin production.

U.S. Pat. No. 4,359,528 describes a process for producing a corn steep liquor which is said to facilitate the lactic fermentation to a maximum and to produce a product having a high concentration of dry matter, an almost total absence of reducing sugars, an extremely regular composition and a very low content of free lysine, histidine, arginine, aspartic acid and tyrosine. The process described in the U.S. patent for achieving these aims comprises contacting corn grains placed in silos arranged in series with a steepwater containing about 0.75 to 3 grams sulphur dioxide per liter, which water is introduced successively into each of the silos in series such that the water traverses the silos one after the other, the volume of steepwater in cubic meters introduced per ton of commercial corn defining a cycling ratio. The temperature of the steepwater is maintained so that the temperature decreases progressively from silo to silo as the water passes through the silos from one to the next, from at the most about 58° C. in the input silo to about 32° C. at the outlet of the silo from which the corn steepwater is recovered. The cycling ratio is maintained between 0.8 and 1.2 cubic meter steepwater per ton of commercial corn and the soak time during which the corn grains and steepwater are in contact is kept between about 24 and 44 hours.

As will be clear from the preceding description, the process of the U.S. patent requires a sophisticated temperature control system and at the lower temperatures there is the possibility of yeast fermentation occurring with the production of alcohol from the sugars present. The disclosure of the U.S. patent does briefly summarize two other solutions which have been proposed to encourage lactic fermentation but dismisses both as not giving satisfactory results.

The first of these two other solutions is said to consist of a complementary incubation in which the steepwater with 6 to 8% of dry matter is sent to a storage tank where it remains between 8 and 24 hours before being evaporated. This dwell time is said to permit more thorough exhaustion of the soluble materials by the lactic bacteria. The batch process is, however, comparatively slow and even more than 24 hours is often required to complete the process. Time periods such as this mean that a corn steeping plant has to be provided with relatively large incubators in which to conduct the process, hence, increasing the capital cost.

The second other solution is said to involve the seeding of the steepwater by means of lactic bacteria which would have the effect of reducing soaking time, the temperature of the soaking being comprised between 45° C. and 50° C. and the water cycling ratio used being 1.4 to 1.8 cubic meters of water per ton of commercial corn.

The process of the present invention does not involve changes to the steeping process itself but comprises a post-treatment of the corn steepwater after it has contacted the corn. It is notable for requiring a relatively short period of time for the treatment, by being operated continuously and by producing a product with an improved color and a very low content of reducing sugars. In addition, when desired, the process may be operated so as to produce a product with a low content of free lysine.

SUMMARY OF THE INVENTION

According to this invention, there is provided a process for the treatment of corn steepwater, which comprises (a) separating the steepwater from the corn;
(b) initially adjusting the pH of the steepwater to at least about 3.5;
(c) maintaining the corn steepwater at a temperature of about 40° C. to about 48° C. for up to 48 hours for development of biomass;
(d) continuously feeding corn steepwater to the developed biomass at a rate such that the residence time is in excess of 4 hours in contact with the biomass at a temperature of about 40° C. to about 48° C., the pH of the steepwater feed being adjusted, at least in the initial stage of continuous operation, to be at least about 3.5; and
(e) separating the corn steepwater from the biomass and reducing its volume by evaporation to give corn steep liquor.

DETAILED DESCRIPTION OF THE INVENTION

"Process biomass" is the mass of microorganisms which develops naturally under the steeping conditions in the corn steepwater and which increases in amount with time. It is these microorganisms which produce the enzymes which cause the changes in the corn steepwater to take place. The biomass exists sufficiently as a separate phase from the corn steepwater for the latter to be capable of flowing at a different velocity so that the biomass may be maintained in more concentrated form while the steepwater continuously flows through. The biomass which is present in the steepwater immediately after it leaves the last corn silo is less than is required for an effective operation of the process of the invention. For this reason, startup of the process involves initial pH adjustment followed by maintenance of the corn steepwater at the required temperature for up to 48 hours until the biomass develops in quantity, preferably to at least five time that amount normally present in the corn steepwater, more preferably to at least ten times. Fresh corn steepwater may then be fed continuously to the biomass while treated water is removed therefrom, the amount of biomass remaining being maintained substantially constant and excess being withdrawn with the treated water. The rate at which corn steepwater is fed to the biomass may be increased as the mass of the latter develops so that whereas initially a residence time of 6 to 48 hours may be required, this may be decreased to an optimum of 6 to 15 hours under steady operating conditions.

The initial adjustment of pH usually involves the addition of an alkali to increase the pH to at least 3.5, preferably 3.75 to 4.5 at the start of the process and during the initial operation in a continuous manner. When continuous operation is established, pH adjustment may be discontinued. Initial adjustment of pH to 3.5 or more is effective to produce a product with improved color and with a very low reducing sugar content. If low free lysine is also required, it is recommended to increase the initial pH to greater than 5.0, preferably to about 5.5. The pH is usually adjusted by the addition of alkali, preferably ammonia or an alkali metal hydroxide, although other alkalis may be used if economically acceptable. Generally, ammonium hydroxide is preferred. At startup of the process, the amount of ammonia added as aqueous ammonia may advantageously be about 2.0 weight % (as 100% $NH_3$ dry basis based on steepwater dry subtance). After startup but during the initial period of continuous operation, however, it has been found appropriate to inject aqueous ammonia continuously into the corn steepwater, preferably 0.5 to 1.0 weight % ($NH_3$ dry basis based on steepwater dry substance). The exact amount to be used will, of course, vary from plant to plant, but may readily be determined from the pH desired.

The process is carried out at a temperature in the range 40° to 48° C. Preferred operation is about 45° C., and plant control of temperature is usually such that the actual temperature of operation varies in the range 45° C. to 48° C.

When fully in operation, the process runs continuously. Continuous operation may be achieved by feeding the corn steepwater to one or more, for example, 2 to 4, tanks in series in which the water flows upwardly through the biomass overflowing from the last vessel and carrying some of the biomass with it but maintaining the mass in the vessels substantially constant.

After treatment by the process of the invention, the corn steepwater is conventionally concentrated, for example, in an evaporator, to give corn steep liquor.

The invention will now be further described with reference to the following example in which all percentages are percentages by weight unless otherwise indicated.

EXAMPLE

Two hundred liters of steepwater from a commercial corn steeping process was placed in a suitable vessel provided with heating means and means for gently agitating the contents. The agitation was adjusted to allow some sedimentation of the biomass so maintaining a relatively constant quantity in the incubator. The free lysine content of the steepwater was 50 mg per ml.

The pH of the steepwater was adjusted to 5.5 by addition of ammonia and the steepwater gently agitated for 48 hours at a temperature of 45° C. After the 48-hour time period, the vessel was fed continuously with fresh steepwater over a period of one month. The steepwater was introduced to the base of the vessel and flowed upwardly through the biomass overflowing at the liquid surface. The residence time of the steepwater in the vessel was gradually reduced by increasing the flow rate. For the first 6 days, the residence time was 24 hours which was subsequently reduced to 14 hours for the 7th to the 12th day, and then to 12 hours from the 13th day to the end of the month.

Ammonia was fed continuously to the steepwater as it entered the vessel. The dosage rate was 1% (based on steepwater dry subtance) which was decreased progressively to 0.7%–0.8% on the 7th day, and to 0.6% on the 14th day. On the 18th day, ammonia addition was stopped.

Samples were taken periodically before and after incubation and were analyzed for reducing sugars and free lysine contents (Table I).

Samples taken before and after incubation were concentrated by evaporation and analyzed for dry substance, reducing sugars, free lysine and color (Table II).

TABLE I

| Time (day) | Before Incubation | | | After Incubation | |
|---|---|---|---|---|---|
| | Reducing Sugars (% d.b.)[a] | Free Lysine (mg/100 ml) | pH (20° C.) | Reducing Sugars (% d.b.)[a] | Free Lysine (mg/100 ml) |
| 1 | 12.7 | 65 | 4.06 | 2.0 | 10 |
| 2 | 12.0 | 55 | 3.96 | 1.0 | 8 |
| 3 | 12.0 | 60 | 3.91 | 1.0 | 15 |
| 4 | 7.7 | 100 | 3.98 | 1.6 | 18 |
| 5 | 7.7 | 68 | 3.97 | 1.6 | 13 |
| 6 | 7.4 | — | 3.98 | 1.3 | 10 |
| 7 | 7.4 | — | 3.86 | 1.3 | 35 |
| 8 | 12.0 | 60 | 3.92 | 2.6 | 58 |
| 9 | 12.0 | 73 | 3.90 | 2.6 | 35 |
| 10 | 11.5 | 50 | 3.88 | 2.2 | 20 |
| 11 | 11.5 | 60 | 3.94 | 2.2 | 10 |
| 12 | 12.7 | 88 | 3.90 | — | 10 |
| 13 | 12.7 | 65 | 3.90 | 2.9 | 23 |
| 14 | 9.0 | 70 | 3.96 | 2.9 | 13 |
| 15 | 9.0 | 70 | 3.86 | 1.0 | 13 |
| 16 | 11.5 | 48 | 3.80 | 1.0 | 13 |
| 17 | 11.5 | 68 | 3.81 | 2.8 | 15 |
| 18 | 8.8 | 50 | 3.86 | 2.8 | 15 |
| 19 | 6.2 | 60 | 3.80 | 3.4 | 20 |
| 20 | 4.7 | 30 | 3.77 | 3.6 | 15 |
| 21 | 11.9 | 90 | 3.78 | 1.5 | 40 |

TABLE I-continued

| | Before Incubation | | | After Incubation | |
|---|---|---|---|---|---|
| Time (day) | Reducing Sugars (% d.b.)[a] | Free Lysine (mg/100 ml) | pH (20° C.) | Reducing Sugars (% d.b.)[a] | Free Lysine (mg/100 ml) |
| 22 | 8.1 | 55 | 3.88 | 5.3 | 25 |
| 23 | 8.4 | 43 | 3.88 | 1.1 | 10 |
| 24 | 10.1 | 55 | 3.78 | 2.4 | 13 |
| 25 | 8.9 | — | — | 3.6 | — |
| 26 | — | — | — | 3.9 | 8 |

[a] Where d.b. = dry basis

TABLE II

| Day | d.s.[a] Content (%) | Free Lysine (mg/100 g d.s.) | Reducing Sugars (% d.s.) | Color |
|---|---|---|---|---|
| Nonincubated Samples | | | | |
| 3 | 50.3 | 632 | 10.6 | Dark |
| 10 | 49.8 | 667 | 9.0 | Dark |
| 14 | 45.8 | 843 | 12.6 | Dark |
| Incubated Samples | | | | |
| 3 | 53.8 | 104 | 1.5 | Pale |
| 5 | 50.9 | 110 | 1.3 | Pale |
| 6 | 50.1 | 218 | 1.5 | Pale |
| 10 | 54.4 | 217 | 1.4 | Pale |
| 14 | 54.2 | 138 | 1.3 | Pale |
| 16 | 50.2 | 109 | 1.4 | Pale |
| 23 | 49.8 | 72 | 1.3 | Pale |

[a] Where d.s. = dry substance

Thus, it is apparent that there has been provided, in accordance with this invention, a process for the treatment of corn steepwater that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for the treatment of corn steepwater, which consists essentially of:
    (a) separating steepwater from corn;
    (b) initially adjusting the pH of the steepwater to at least about 3.5;
    (c) maintaining the steepwater at a temperature of about 40° C. to about 80° C. for up to 48 hours for development of biomass;
    (d) continuously feeding fresh steepwater to the developed biomass at a rate such that the residence time is in excess of 4 hours in contact with the biomass at a temperature of about 40° C. to about 48° C., the pH of the steepwater feed being adjusted, at least at the beginning of the continuous feeding, to be at least about 3.5; and
    (e) separating the steepwater from the biomass and reducing its volume by evaporation to give corn steep liquor.

2. The process of claim 1, wherein the quantity of biomass developed in Step (c) is at least five times the amount present in Step (b).

3. A process according to claim 1, wherein the pH is adjusted to 3.75 to 4.5 in Step (b).

4. A process according to claim 1, wherein the pH in Step (b) is greater than 5.

5. A process according to claim 4, wherein the pH is about 5.5.

6. A process according to claim 4, wherein the pH is adjusted by the addition of ammonia.

* * * * *